United States Patent [19]
Moran

[11] 4,058,002
[45] Nov. 15, 1977

[54] DISPERSIVE ELECTROMAGNETIC SURFACE ACOUSTIC WAVE TRANSDUCER

[75] Inventor: Thomas J. Moran, Dayton, Ohio

[73] Assignee: The United States of America as represented by the Secretary of the Air Force, Washington, D.C.

[21] Appl. No.: 753,967

[22] Filed: Dec. 23, 1976

[51] Int. Cl.² .......................................... G01N 29/00
[52] U.S. Cl. ..................................... 73/620; 340/15; 73/629
[58] Field of Search .......... 73/67.8 R, 67.8 S, 67.5 R, 73/67.7; 340/15; 336/110, 224, 232

[56] References Cited

U.S. PATENT DOCUMENTS

| 1,816,448 | 7/1931 | Terman | 336/224 |
|---|---|---|---|
| 3,550,435 | 8/1967 | Kaule | 73/67.8 R |
| 3,786,672 | 1/1974 | Gaerttner | 73/67.8 R X |

Primary Examiner—Jerry W. Myracle
Attorney, Agent, or Firm—Joseph E. Rusz; Robert Kern Duncan

[57] ABSTRACT

A surface acoustic wave electromagnetic transducer (SAW EMT) having a meander line with progressively smaller spacing between conductors produces a surface, acoustic, traveling, exploratory, output signal that is greatly dispersed, when excited with a pulse electrical signal; and a corresponding compressed electrical output signal is produced from a received acoustic signal. The transducer may be used either to transmit or receive signals.

7 Claims, 16 Drawing Figures

Fig-1 PRIOR ART WAVE SHAPE

DISPERSIVE ELECTROMAGNETIC SURFACE ACOUSTIC WAVE TRANSDUCER

RIGHTS OF THE GOVERNMENT

The invention described herein may be manufactured and used by or for the Government of the United States for all governmental purposes without the payment of any royalty.

BACKGROUND OF THE INVENTION

The field of the invention is in the nondestructive testing art and more particularly in acoustic surface wave transducers for nondestructive surface examination.

Figure 1:
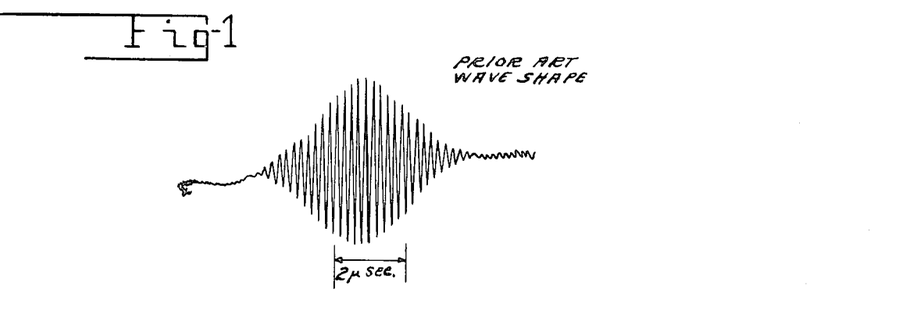
FIG. 1 is a typical waveform of prior art devices.

Recent advances in the design of, and the electronics for, electromagnetic SAW transducers (SAW EMTs) have increased the dynamic range of these devices to the point where they are comparable in sensitivity to piezoelectric wedge transducers for NDE inspections of metals such as aluminum or magnetic steels. One remaining problem which, prior to this invention, has hindered the application of SAW EMTs to NDE problems is poor range resolution. This difficulty arises from the fact that the transduction efficiency is proportional to the square of the number of periods in the meander line. Practical devices usually have meander lines with 5 to 20 periods. When such a device is excited by a short pulse, the resulting output tone burst is NT long where N is the number of periods and T is the period. When an identical meander line is used to receive the generated tone burst, the burst is spread by an additional NT. Thus, it is not generally possible to generate and detect tone bursts of less than approximately 2NT duration with conventionally designed SAW EMTs. The problem is illustrated in FIG. 1 where the response of a transmitter-receiver pair of 16 period 5 MHz SAW EMTs to a 50 nsec pulse excitation is shown. The received tone burst in this case is 6 μsec long (corresponding to a spatial extent of 1.8 cm). Such a pair of transducers would be virtually useless for a conventional ultrasonic NDE inspection if it were necessary to find flaws less than 1 cm apart or within 1 cm of an obstacle such as a bolt hole.

For additional background that may be helpful in understanding the present invention, attention is directed to the paper, IEEE Cat. No. 76 CH1120-55U presented at the 1976 Institute of Electrical and Electronic Engineers Ultrasonics Symposium, Sept. 29 to Oct. 1, 1976, entitled "Use of Pulse Compression Techniques to Improve the Range Resolution of Electromagnetic Surface Wave Transducers" by T. J. Moran. The following patents may be helpful in illustrating the prior art. U.S. Pat. Nos. 3,460,063 to patentees J. R. Houck et al, 3,550,435 to patentee W. Kaule, 3,786,672 to patentee M. R. Gaerttner, and 3,850,028 to patentees R. B. Thompson et al.

SUMMARY OF THE INVENTION

Typical surface acoustic wave electromagnetic transducers fabricated according to the examples disclosed herein will resolve surface defects that are only approximately 0.50 mm apart, a great improvement over the prior art SAW EMT devices. Embodiments of the invention may be fabricated to provide optimum performance in various materials and with resolution capabilities in accord with the magnitude of flaw detection desired. The transducer is relatively easy to fabricate and it is completely reproducible, one of the major problems of present state of the art piezoelectric devices.

BRIEF DESCRIPTION OF THE DRAWING

FIG. 3b is a representative side view of FIG. 3a;
FIG. 6 illustrates schematically in a side section view the relationship of the meander line and magnet structure of the embodiment shown in top view in FIG. 5.

DESCRIPTION OF THE PREFERRED EMBODIMENTS

Figure 2:
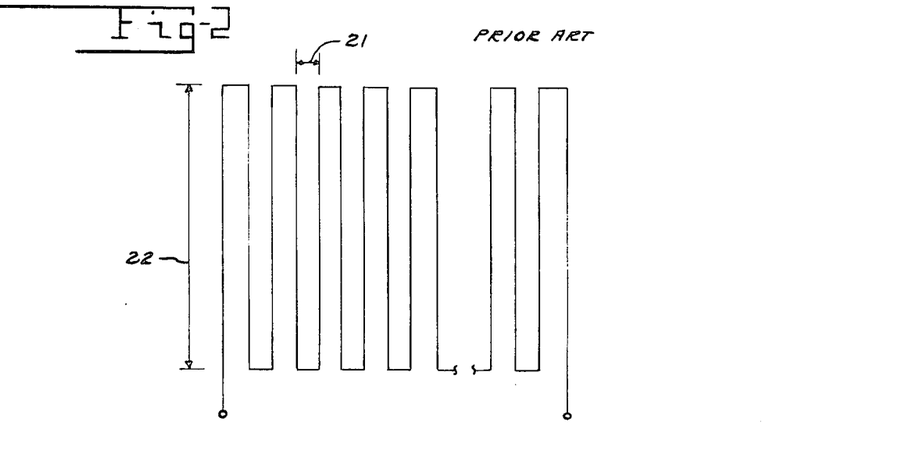
FIG. 2 illustrates schematically a conventional prior art meander line.

Fundamentally electromagnetic transducers for surface acoustic waves consist of two major parts; a dc magnetic field and a current carrying conductor. Current state of the art transducers generally use high energy-product permanent magnets, such as a rare earth cobalt (e.g., Sm—Co), to establish a strong magnetic field, and a printed circuit conductor. The conventional printed circuit "coil" in the current transducers is illustrated in FIG. 2. The component of the magnetic field in the plane of the printed circuit coil acts to produce the acoustic waves. The coil is frequently referred to as a meander line. "Serpentine" is also sometimes used to describe the coil of SAW EMTs. The conventional coil as illustrated in FIG. 2 has uniform spacing 21 between conductors. This spacing equals ½ the wavelength of the generated acoustic wave. The acoustic beam width is substantially the length 22. When a conventional SAW EMT having a conventional coil as illustrated in FIG. 2 is driven by an electrical pulse a SAW as illustrated in FIG. 1 is produced.

Figure 3A:
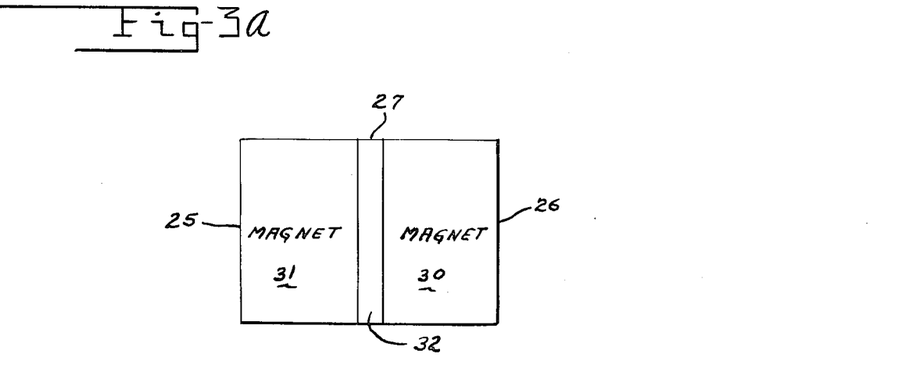
FIG. 3a illustrates a top view of a typical single transducer magnet structure.
Figure 3B:
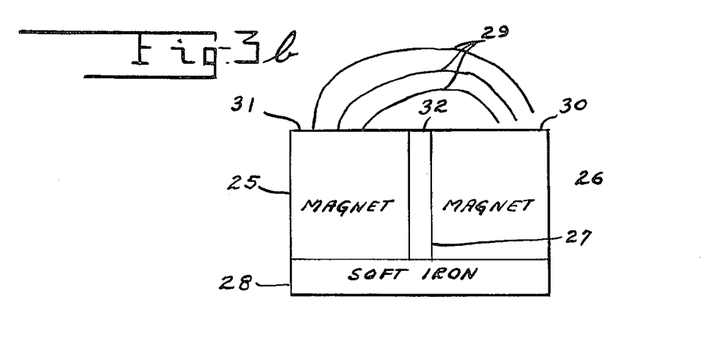

The dispersive surface acoustic wave electromagnetic transducer as disclosed herein also consists of two principal parts; the printed circuit coil and the permanent magnet structure. The magnetic structure of devices of this invention is similar to the conventional SAW EMT magnetic structure as illustrated in FIGS. 3a (top view) and 3b (side view). Conventional high energy permanent magnets 25 and 26, separated by magnetic insulator 27, with a magnetic shunt 28 joining opposite poles of the magnets 25 and 26, provide a magnetic field 29. The driving (and detecting) coil is placed in this magnetic field close to the plane surface formed by the surfaces of the magnets 30 and 31, and 32 of the insulator.

Figure 4:
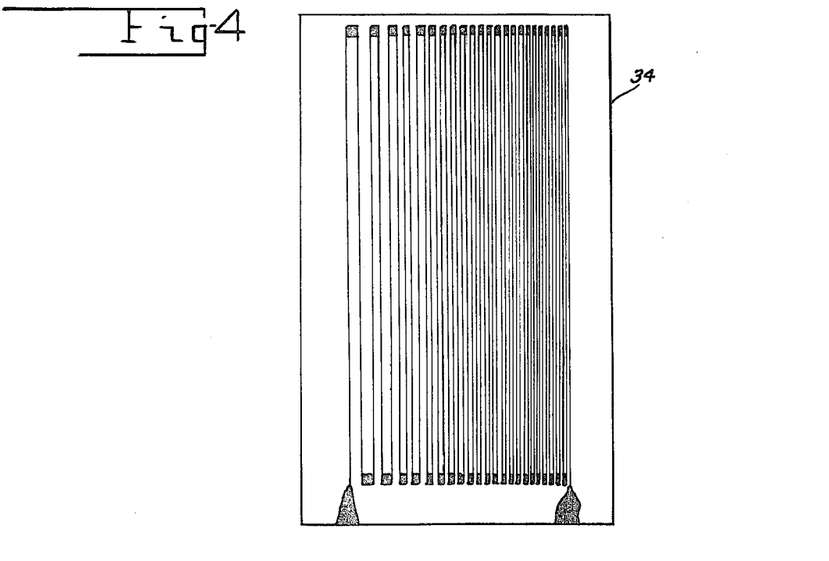
FIG. 4 illustrates an embodiment of an improved meander line.

The dispersive transducer of this invention has a printed circuit coil 34 fabricated as illustrated in FIG. 4. The spacing between the conductors is no longer constant, but is now a function of position according to the following equation:

$$(\Delta f/\Delta t)x^2 + f_o vx - \tfrac{1}{2}Nv^2 = 0$$

where $N$ is an integer which corresponds to the number of the conductor whose position is being calculated. $f_o$ is the lowest frequency to be generated ($\Delta f/\Delta t$) is the rate at which the frequency is to be changed, $v$ is the velocity of the surface acoustic wave and $x$ is the position of conductor number N.

The printed circuit coil is conventionally constructed using standard photographic printed circuit techniques, i.e., a large scale drawing is made, a high contrast negative is made of the drawing and a positive print is made on a photographic emulsion coated copper clad printed circuit board. For electromagnetic transducers which operate in the MHz frequency range, it is best to use a printed circuit board which has a very thin backing for the copper. The copper also should preferably be no more than 2 mil thick. A commercially made flexible printed circuit board which consisted of 2 mils of copper on a 4 mil mylar substrate was found to operate very well.

Figure 5:
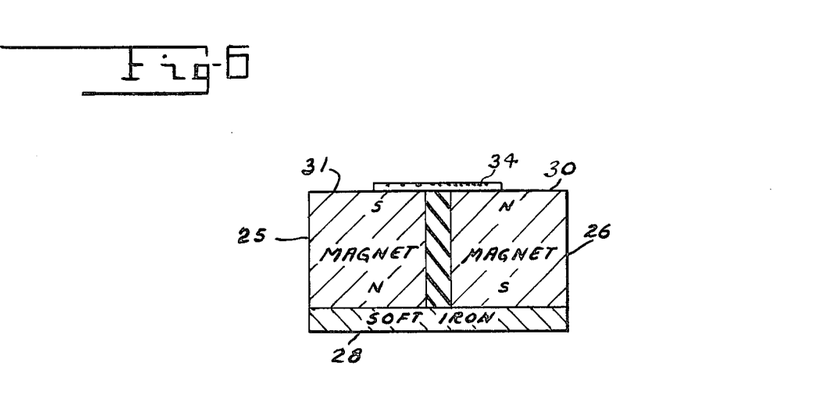
FIG. 5 illustrates schematically a top view of the placement of the meander line and the magnet in a typical embodiment of the invention.

A meander line as illustrated in FIG. 4 was fabricated for operation with aluminum with frequencies between 2 and 6 MHz, and with a pulse width of 3.5 μsec. The final dimensions of the active area of this meander line were 1.1 cm × 2.2 cm. The line was mounted between the poles of a horseshoe shaped Sm—Co permanent magnet. The magnet and meander line were then mounted in the holder 35 as shown in FIG. 5. The active elements of the embodiment, as illustrated pictorially in FIG. 5, are shown in vertical section in FIG. 6. Generally it is desirable that the width of the magnetic structure be approximately twice the width of the active coil elements.

Figure 12:
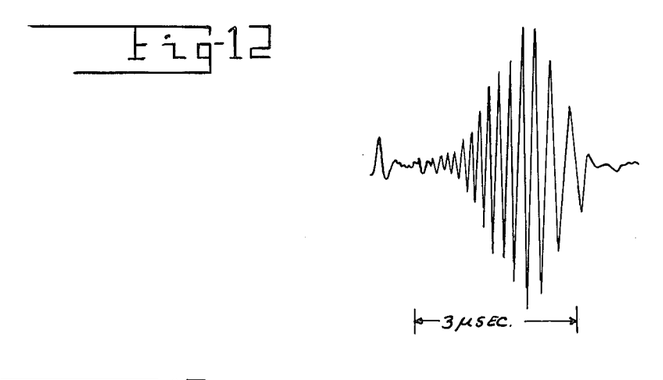
FIG. 12 illustrates a typical chirp traveling surface acoustic wave generated by a pulse applied to an embodiment of the invention.

When this particular embodiment of a dispersive SAW EMT is pulse excited with a 50 nsec pulse, an output chirp signal such as is shown in FIG. 12 is generated in an aluminum surface. In this case the total pulse length is about 3.5 μsec, but the envelope is no longer square due to the variation of the static magnetic field with position. When this chirp signal is recompressed by a receiving dispersive SAW EMT, the resulting output shown in FIG. 13 has a width of less than 0.25 μsec and a compression ratio of 14 is achieved. This type of excitation where a pulse excites the transmitter and a pulse output is obtained from the receiver corresponds to the pitch-catch mode of operation which is very useful for NDE applications.

Figure 7:
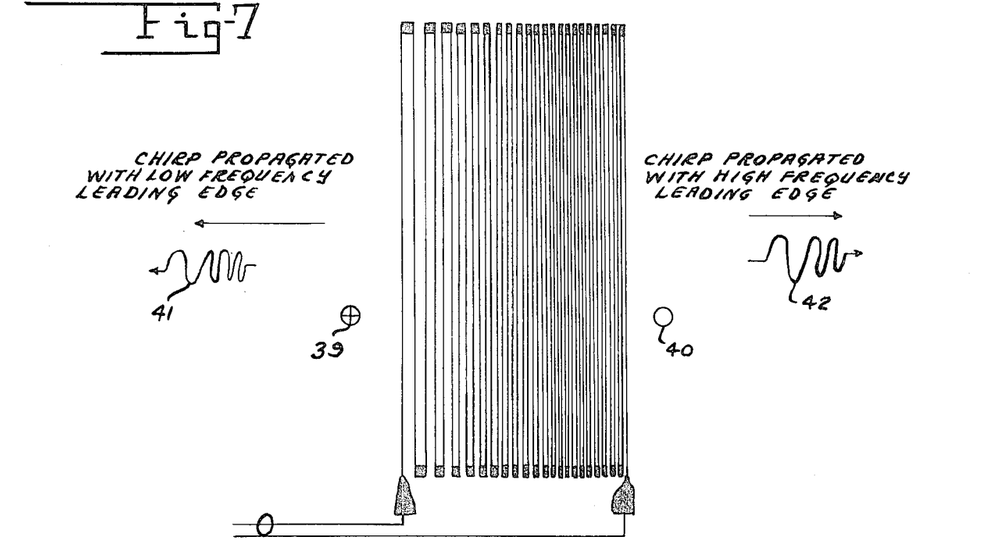
FIG. 7 illustrates a typical transmitted response to an electrical pulse of the meander line and magnet structure of FIGS. 6 and 7.
Figure 10:
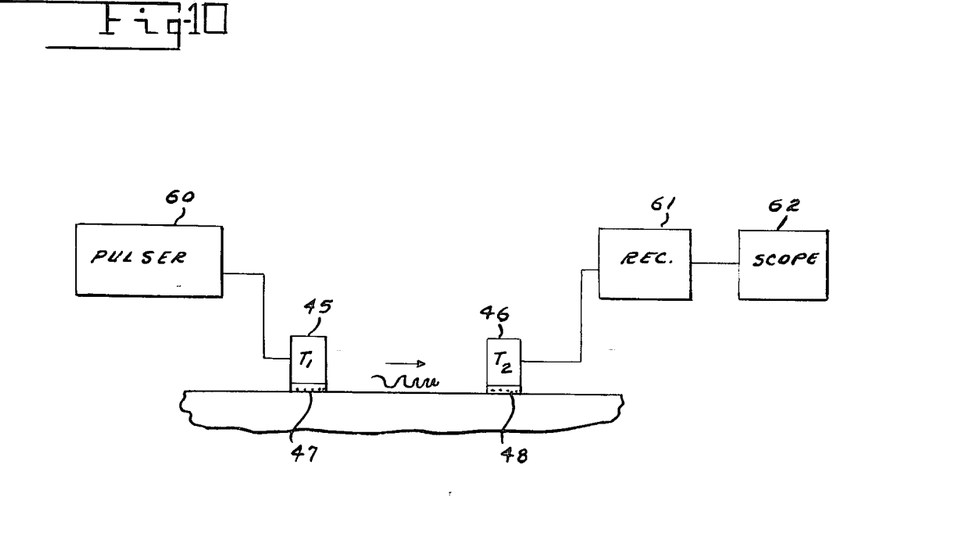
FIG. 10 illustrates schematically a typical equipment setup utilizing two separate transducers for examining a surface.

FIG. 7 illustrates that chirp acoustic waves, one ascending, one descending in modulation frequency, are produced in both directions from the transducer. The polarity of the magnetic field 39–40 is immaterial, resulting in a phase reversal only of the output waves 41 and 42. Likewise, either wave may be used in exploratory operations. It is imperative that in the receiving SAW EMT that the coil spacing progression match the rising or falling frequency characteristic of the surface acoustic wave passing under the receiving transducer. Thus, when two substantially identical transducers 45 for generating a signal and 46 for detecting a signal, are used for surface examination as illustrated in FIG. 10, the progression of the spacing in the coils must be as schematically illustrated 47 and 48, (or both reversed). That is, the rate of change of conductor spacing in each transducer is in the same direction along a common direction line.

Figure 8:
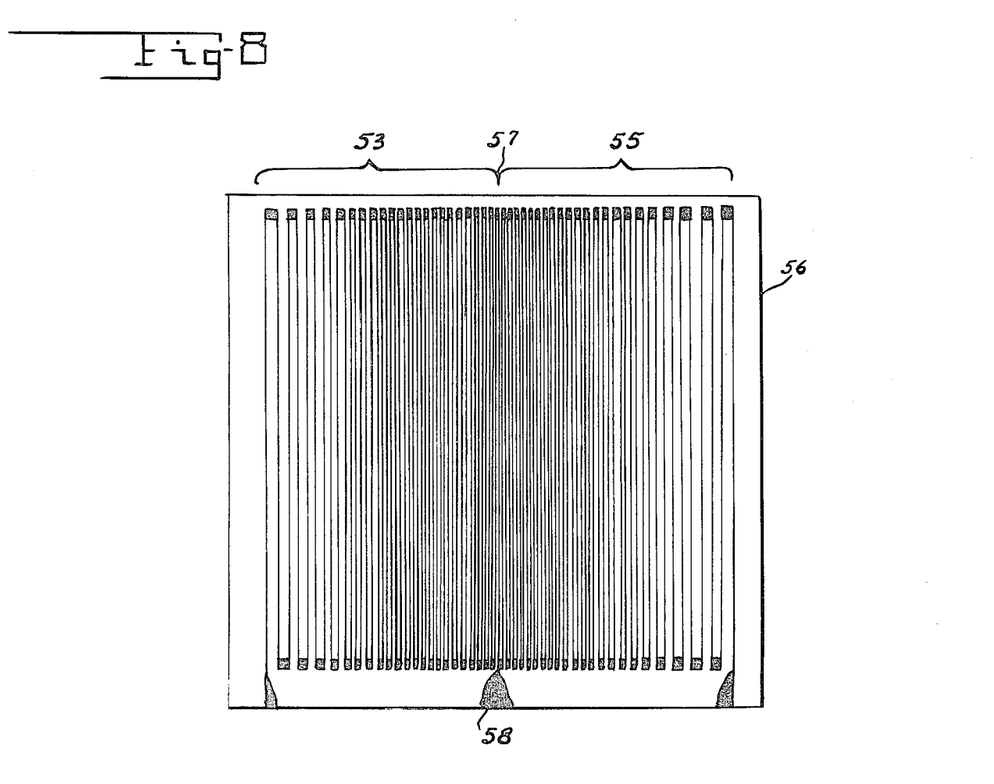
FIG. 8 illustrates a dual meander line for both transmitting and receiving from a dual transducer.
Figure 9:
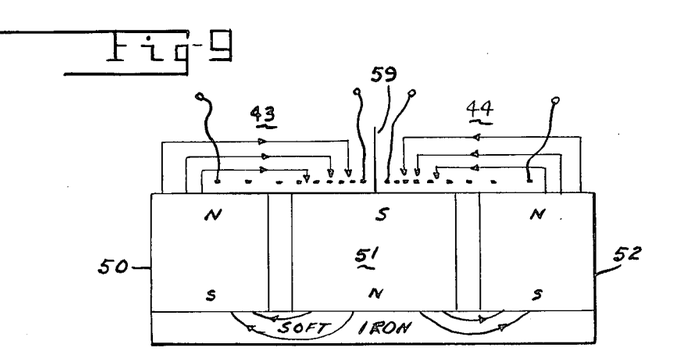
FIG. 9 illustrates schematically the positioning of the dual meander line of FIG. 6 and a dual magnetic structure in a typical embodiment of the invention for both transmitting and receiving in a single transducer unit.

In many instances it is desirable to use one transducer assembly unit in an echo-ranging mode for testing purposes. From the foregoing discussion it is apparent that a single transducer such as previously illustrated cannot be used in this mode, without turning the transducer around between the time of the transmitted and received signals. A very impractical operation! Thus, a dual transducer having both a transmitting and a receiving section is required. A dual meander line 56 as illustrated in FIG. 8 comprising two meander lines 53 and 55, identical, except one is reversed frequency progression wise with respect to the other, is positioned over a dual magnet structure as illustrated in FIG. 9. The conductor spacing of the meander line 56 progressively changes in both directions from the center 57 of the line at an equal and determined rate as previously set forth. The low frequency spacing may be positioned at the center of the line instead of the high frequency spacing with equivalent results. Instead of a common connection 58 at the mid point of the line, separate connections may be brought out as illustrated in FIG. 9. This embodiment is conventionally typically positioned in a holder like the single transducer embodiment so that it can be conveniently hand-held and readily moved over the surface being inspected. The absolute polarities of the magnets 50, 51, and 52 are immaterial other than they cooperate magnetically as illustrated. The fact that in operation there may be a phase reversal between the two sections is unimportant. The peak of the output electrical pulse would merely be shifted in time equivalent to one-half cycle of the lowest frequency component of the wave. A typical magnet structure, as illustrated in FIG. 9, for the dual transducer, has two magnetic fields 43 and 44 substantially of opposite direction both magnetically and physically about the midpoint 59 between the two fields.

Figure 11:
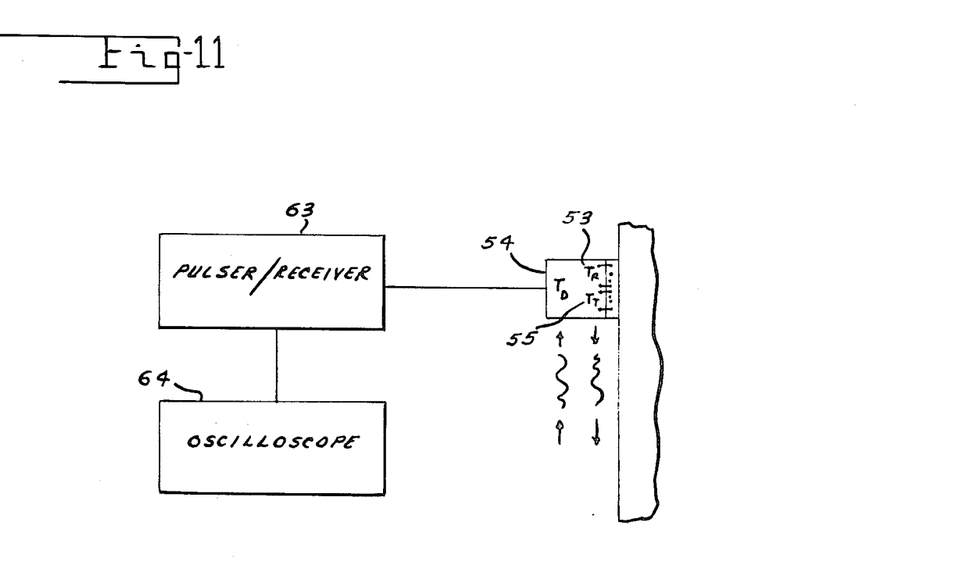
FIG. 11 illustrates schematically a typical equipment setup for surface examination with a typical dual transducer embodiment of the invention.

A typical system of cooperating electronic equipment associated with the dual transducer is illustrated in FIG. 11. It is to be noted that with the conventional prior art SAW EMT having a coil with uniform spacing that the same transducer may be used for both sending and receiving, or two separate ones may be used. With the dispersive transducers of this invention, separate transmitting and receiving transducers 52 and 53 (even though they are both contained in one assembly 54) must be used as was previously explained.

The electronic systems 60 through 64 for generating, receiving, and displaying the signals of the SAW EMTs of this invention may be conventional commercial units as used with prior art devices. Due to the greater resolution made possible by this invention it is preferable that the better commercial units be used so as to be able to take full advantage of the greatly improved transducers.

Figures 13, 14:
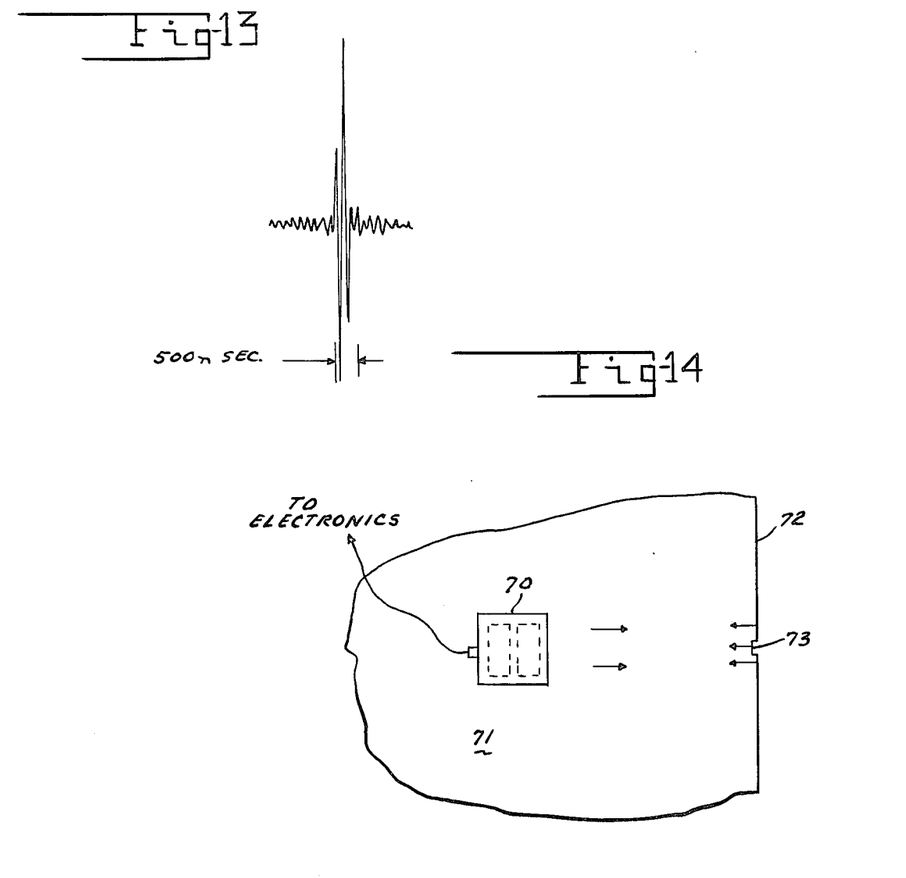
FIG. 13 illustrates the electrical output response from a typical embodiment of the invention to the surface acoustical wave shown in FIG. 10.
FIG. 14 schematically shows a typical operation illustrating the resolution capabilities of a typical dual transducer.
Figure 15:
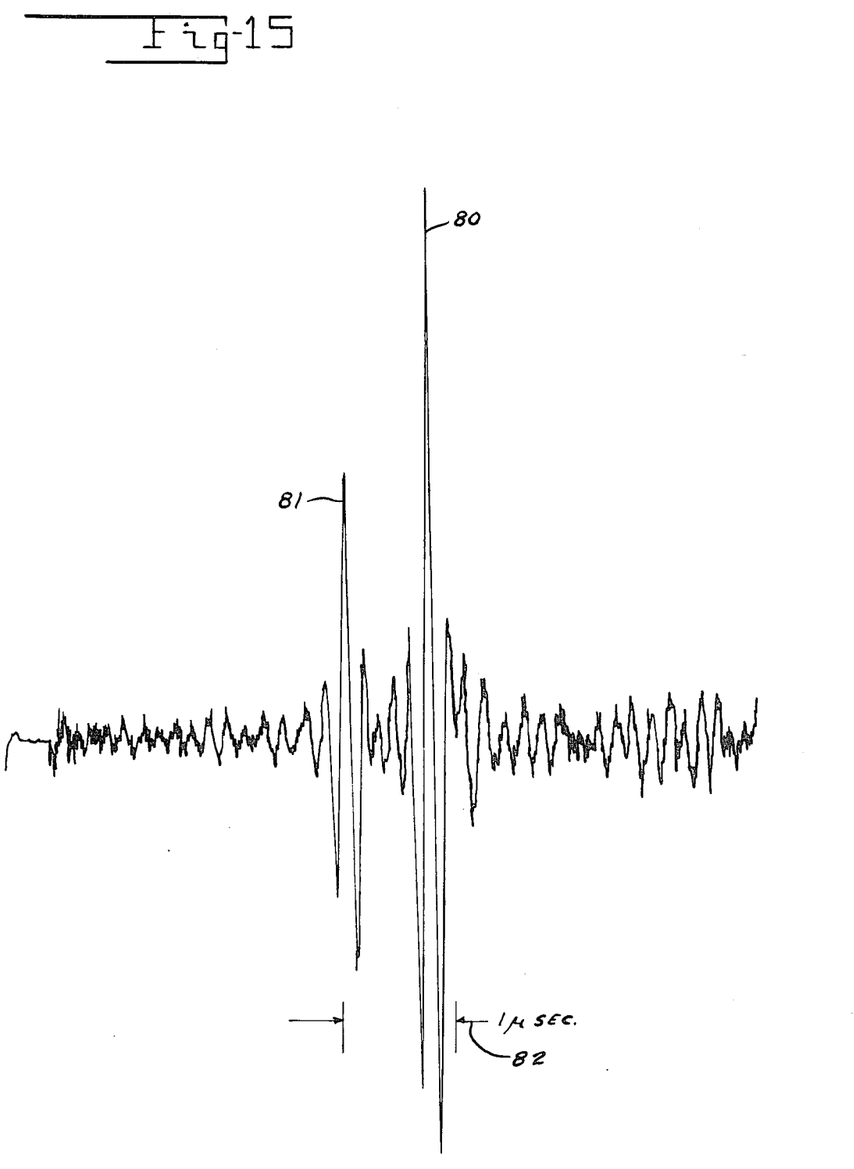
FIG. 15 is a typical waveform provided by a dual embodiment of the invention illustrating typical resolution to a notch in an edge as shown in FIG. 14.

A typical setup showing the typical resolution characteristics of a dual transducer unit is illustrated in FIGS. 14 and 15. The dual transducer 70 is positioned on an aluminum surface 71 approximately 8 centimeters from edge 72. The transmitting section was driven with approximately a 50 nanosecond electrical pulse. The notch 73 in the edge is approximately 1.09 mm from the back surface. (The figure is illustrative and not to scale.) FIG. 15 is an x-y recording of the signal obtained with the foregoing described embodiment and associated electronic equipment in the operation shown in FIG. 14. The return reflection from the edge 72 is the pulse associated with spike 80. The return reflection from the notch 73 is the spike and pulse 81. The reference spacing 82 is 1 microsecond. It is very plain that the small notch in the edge can easily be resolved from the edge reflection.

To aid in the practice of this invention it may be desirable to consider the following parameters and characteristics. As is common practice with EMTs, it is frequently desirable to place a tuning capacitor across the coil of the EMT or use an impedance matching transformer to properly match it to the driver and receiver. The transducer must be placed in close proximity to the surface being examined. Conventionally, a 1 to 3 mill sheet of Mylar may be placed over the surface being examined with the transducer or transducers resting on the Mylar.

The reciprocity characteristic of the dispersive transducer of this invention should be noted. Generally, for NDE usage a dispersive transducer is driven by a short electrical pulse. The acoustic surface wave then produced will be a relatively long rf burst which is frequency modulated with the rate of change of the frequency being equal to the equivalent design rate fabricated in the meander line. When a second dispersive transducer is used to receive the acoustic wave, its output will substantially reproduce the original short electrical pulse. Now, if the dispersive transducer is excited by a frequency modulated rf burst where the modulation rate is equal to the design rate fabricated into the meander line, the acoustic output will be a compressed pulse whose width will be compressed by the factor $\Delta f$ times $\Delta t$ where $\Delta f$ is the total change in drive frequency and $\Delta t$ is the time for an acoustic wave to travel across the transducer. A second dispersive transducer receiving the pulse will re-expand it and substantially reproduce the drive rf frequency modulated burst.

I claim:
1. A dispersive surface acoustic wave electromagnetic transducer comprising:
   a. means for providing a magnetic field; and
   b. a meander line coil having conductors with progressively changing spacing between conductors at a predetermined rate of change of spacing, positioned in the said magnetic field.

2. The transducer as claimed in claim 1 wherein the said rate of change of the said spacing is substantially determined by the expression $(\Delta f/\Delta t)x^2 + f_o vx - \frac{1}{2}Nv^2 = 0$ where $N$ is an integer which corresponds to the number of the conductor whose position is being calculated, $f_o$ is the lowest frequency to be generated, $\Delta f/\Delta t$ is the rate at which the frequency is changed, $v$ is the velocity of the surface acoustic wave, and $x$ is the position of the conductor number N.

3. A nondestructive surface examining system comprising:
   a. a first dispersive surface acoustic wave electromagnetic transducer having a permanent magnet field and a meander line coil with a predetermined rate of change of conductor spacing positioned in the said field; the said transducer positioned on the said surface for generating a surface acoustic wave;
   b. a second dispersive surface acoustic wave electromagnetic transducer substantially identical with the said first transducer positioned on the said surface for detecting a surface acoustic wave;
   c. means including an electronic pulser for driving the said first transducer; and
   d. means including a receiver and an oscilloscope cooperating with the said second transducer for displaying the said received surface acoustic wave.

4. The system as claimed in claim 3 wherein the rate of change of conductor spacing in the said first transducer and in the said second transducer are in the same physical direction and substantially in a common direction line.

5. An electromagnetic dual transducer dispersive surface acoustic wave device for generating a surface acoustic wave in a metallic surface and detecting a resulting reflected surface acoustic wave, the said dual transducer comprising:
   a. a permanent magnet structure providing a magnetic field;
   b. a meander line with conductor spacing progressively changing in spacing at a determined and equal rate in both directions from the center of the said meander line; and
   c. means for positioning the said meander line in the said field.

6. The dual transducer as claimed in claim 5, wherein the said permanent magnet structure provides a first magnetic field and a second magnetic field, the direction of the said second magnetic field being substantially opposite in direction to the said first field, with a mid position between the two fields.

7. The dual transducer as claimed in claim 6 wherein the said center of the meander line is positioned substantially at the said mid position between the said two magnetic fields.

* * * * *